United States Patent
Coleman et al.

(10) Patent No.: US 7,048,690 B2
(45) Date of Patent: May 23, 2006

(54) PRECISION ULTRASOUND MEASUREMENT FOR INTRAOCULAR LENS PLACEMENT

(75) Inventors: Jackson D. Coleman, Haworth, NJ (US); Ronald J. Silverman, Nyack, NY (US); Mark J. Rondeau, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 69 days.

(21) Appl. No.: 10/478,319

(22) PCT Filed: Mar. 19, 2002

(86) PCT No.: PCT/US02/08817

§ 371 (c)(1),
(2), (4) Date: Jun. 9, 2004

(87) PCT Pub. No.: WO02/074248

PCT Pub. Date: Sep. 26, 2002

(65) Prior Publication Data

US 2004/0210139 A1    Oct. 21, 2004

Related U.S. Application Data

(60) Provisional application No. 60/277,061, filed on Mar. 20, 2001.

(51) Int. Cl.
*A61B 8/06*        (2006.01)
(52) U.S. Cl. .................................... 600/452
(58) Field of Classification Search ............... 600/437, 600/438, 440–452; 73/625, 626; 351/159, 351/160 R, 177, 205, 206, 212; 382/103; 606/4, 10, 107
See application file for complete search history.

(56) References Cited

U.S. PATENT DOCUMENTS 5,387,180 A * 2/1995 Lehmer .......................... 601/2
6,053,613 A * 4/2000 Wei et al. ................... 351/205

* cited by examiner

Primary Examiner—Ali Imam
(74) Attorney, Agent, or Firm—Nixon Peabody LLP

(57) ABSTRACT

Visual displays of the geometry and/or topography of a portion of the eye is obtained from data generated during a number of angularly spaced scans taken across a meridional coronal section or of a marginal sector of the anterior surface of the eye, the data being processed for display, to thereby permit the optimization of the surgical placement and the configuration of lenses.

14 Claims, 4 Drawing Sheets

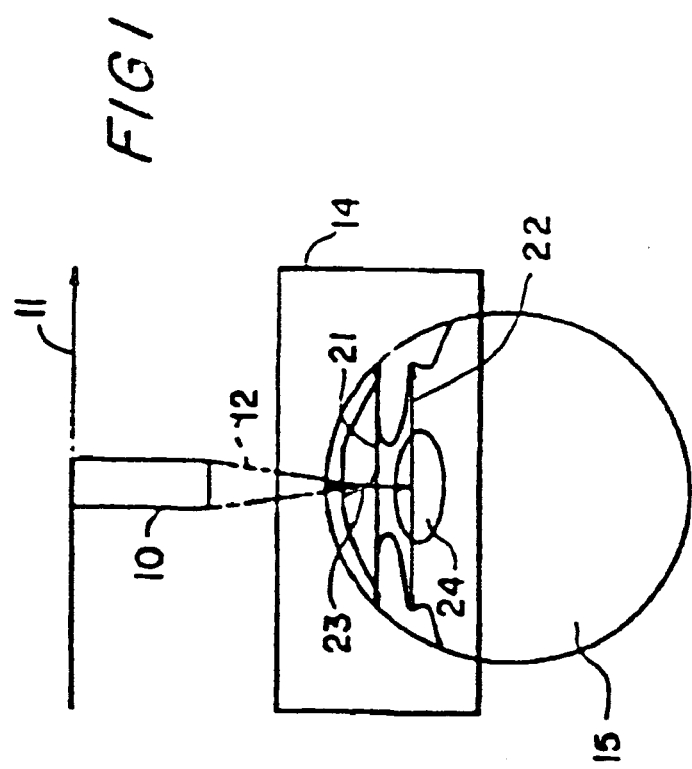
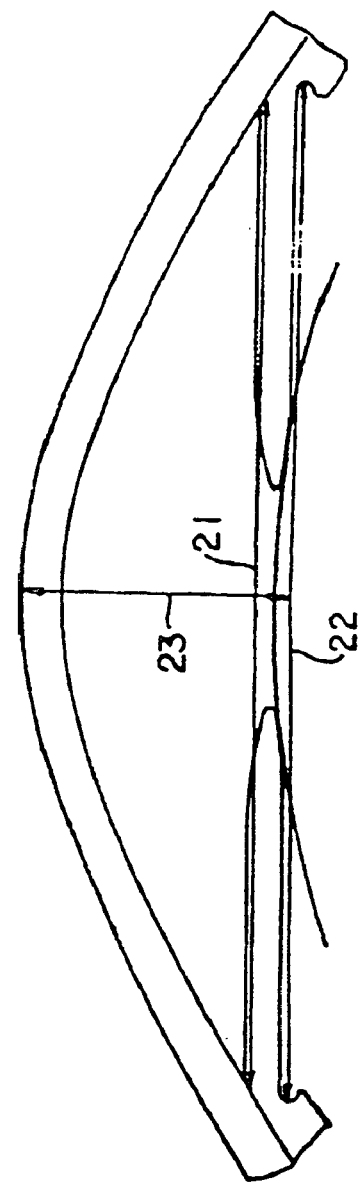

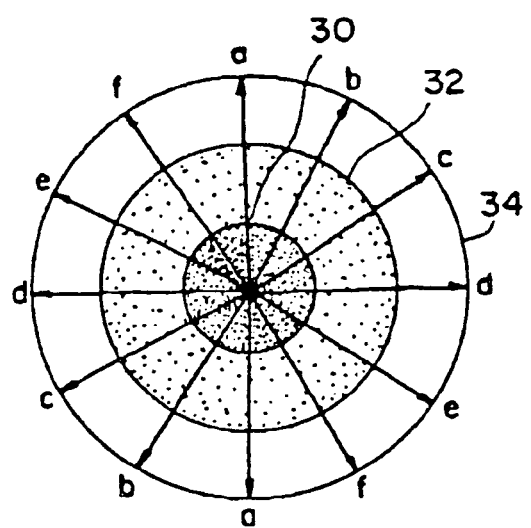
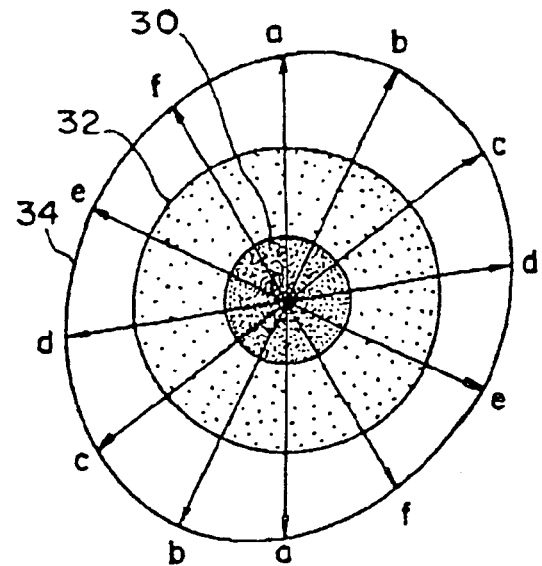
FIG.3A          FIG.3B
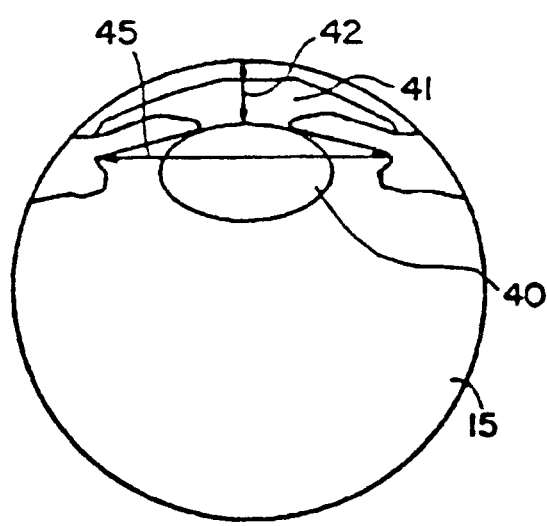
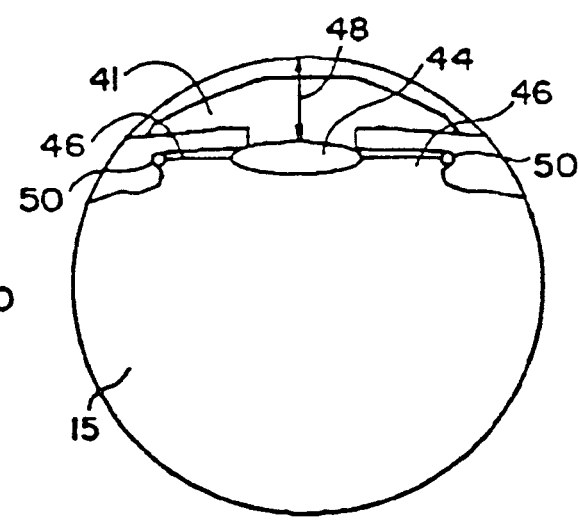
FIG.4A          FIG.4B

PRECISION ULTRASOUND MEASUREMENT FOR INTRAOCULAR LENS PLACEMENT

RELATED APPLICATIONS

This application is the U.S. National Phase under 35 U.S.C. § 371 of International Application PCT/US02/088 17, filed Mar. 19, 2002, which claims priority of 60/277,061, filed Mar. 20, 2001. Each of the above applications is incorporated herein by reference in their entirety.

This invention was made with United States Government support from the National Institutes of Health (NIH) under Grant No. EY01212. The United States Government has certain rights in the invention.

FIELD OF INVENTION

This invention relates to a method of collecting, processing and displaying data that is generated during the scanning of the eye utilizing high-frequency ultrasound scanning apparatus and associated devices.

BACKGROUND OF THE INVENTION

Information obtained by high-frequency ultrasound scans of the critical optical dimensions of the human eye have not been fully utilized to more accurately depict the geometry and/or the topography of the relevant portions of the eye in preparation for lens implantation and/or lens replacement in the case of cataract removal. An improved method of providing measurements with a graphical and/or visual display of the eye for use by technicians and surgeons in preparation for the surgery is required. Improved methods of post-surgical evaluation of the positioning of the lens is also needed.

It is therefore an object of this invention to provide an improved method of collecting, processing and displaying data and graphic information derived from ultrasound scanning of the eye to more accurately depict the geometry and/or the topography of the eye.

It is a further object of the invention to provide this information in a format that can be utilized by the surgeon to improve the positioning of the lens and by those those responsible for providing the implant lenses so that lens design can be optimized for each subject.

Another object of the invention is to provide data and graphic displays in a form that can be utilized to improve the design and manufacture of lenses that more closely conform to the actual geometry of the subject's eye than are currently available.

Another important finding is that previous assumptions are not correct hat the flatter corneal meridian defined the greatest diameter internal axis.

SUMMARY OF THE INVENTION

The method of the invention provides new graphical representations and measurements, as well as visual displays of coronal sections or segments that represent cross-sectional views of the relevant portion of the eye to permit the selection of a lens having the proper power.

These visual displays and graphical representations also provide information not previously available to determine the geometry of the sulcus and angle. Prior art methodology and surgical procedures assumed that the relevant portion of the eye was circular so that the particular orientation of the lens was not critical. Using the method of data collection and processing of the invention, the relevant portion can be shown to be of oblate configuration and the position of the oblate meridian is precisely determined and revealed. This display and information permits surgical placement of the lens in the optimum position.

In a further preferred embodiment of the invention, the number of meridional scans is increased to further define the interim margins or edges of the in-plane surface.

The method of the invention is also used to evaluate any post-placement hazards due to movement of the lens during and following surgery. This adjustment phase may occur over a period extending for more than six-months, during which the lens can move to cause discomfort to the patient and to create a risk of damage to the iris or other elements of the eye. Utilizing the method of the invention, appropriate coronal scans gather data across the entire iris, i.e., from angle-to-angle and sulcus-to-sulcus The above objects and other advantages are obtained by the method of the invention which includes the steps of:

1. providing a very high-frequency ultrasound scanning apparatus;
2. positioning the patient's eye on which lens implanting and/or replacement is contemplated in position for scanning;
3. scanning the patient's eye to thereby generate data representative of a plurality of angularly spaced meridional coronal sections, or meridians, taken across the entire plane of the anterior surface of the eye;
4. collecting, storing and processing the coronal scan data to identify the longest coronal meridian;
5. displaying a graphical plot of the longest coronal meridian; and
6. processing data from a predetermined number of other coronal sections and providing a display of their length and position relative to the longest coronal meridian and a graphic plot and measurements of the 3-D conformation of the subject's eye.

The invention further comprehends a method of producing for visual display a representation of the geometry or the topography, or both the geometry and topography of a portion of the eye, of a subject which representation is based on data generated by an ultrasound scan of the optical components of the eye, the method comprising the steps of:

a. providing a very high-frequency ultrasound scanning apparatus that includes a programmed computer and ancillary data storage device;
b. positioning the subject's eye relative to the apparatus for scanning;
c. scanning the subject's eye to thereby generate data representative of a plurality of angularly spaced meridional coronal sections taken across the entire plane of the anterior surface of the eye;
d. collecting and storing the data obtained in step (c) in the ancillary data storage device;
e. processing the coronal scan data; and
f. generating for visual display a representation of a portion of the geometry or topography, or both the geometry and topography of a portion of the subject's eye.

The method of the invention also comprehends processing the data from the scans to provide a cross-sectional representation of the anterior segment of the eye. From this visual display and the data collected, information can be derived to provide measurements of the eye including the following:

1. sulcus plane depth;
2. angle-to-angle width; and
3. sulcus-to-sulcus width.

The method of the invention has the advantages of providing greater accuracy in determining the lens plane position and results in a much better evaluation of the correct lens power required and its placement during surgery.

The method of the invention also comprehends providing data in tabular or graphic form of coronal dimensions that include the angle-to-angle and the sulcus-to-sulcus measurements through 360°. This three-dimensional evaluation permits the largest diameter to be determined and its dimension to be precisely ascertained. As a result, the lens haptics, as well as the shape and overall conformation, can be correctly sized for the largest diameter of the coronal ring, as well as any irregular marginal configurations thereby preventing "propellering" of the lens following surgery.

The method of the invention can also be utilized to prepare for lens replacement procedures. Because cataractous lenses are usually enlarged, preoperative measurements of the anterior chamber depth do not reflect post-operative anterior chamber depth, and hence, proper lens depth. However, because the implant is placed in the sulcus plane, preoperative measurement of sulcus plane depth in accordance with the method of the invention provides a basis for an accurate evaluation of the postoperative positions of the optically refractive elements of the eye. Fire operative measurements of the sulcus plane dimensions are used to insure appropriate sizing and positioning of the implant lenses subsequent to removal of a cataractous lens. The data collected is pressed utilizing appropriate software for that purpose. The resulting information in the form of data or a graphic display, is utilized to prepare a prescription for the implant lens power that is based on corneal curvature, axial length and sulcus depth.

The availability of this data will also allow cylinder corrections to be included in the lens design and provide for improvement in haptic design. This new dimensional information and the ability to record accurate anterior chamber depth measurements for the placement of the lens provides the further specific advantage of greater precision in determining the most appropriate power for the lens. The computation of this corrective lens information utilizes variations of the traditional Colenbrander formula and others, and also permits an improved evaluation of existing lens power for greater accuracy.

BRIEF DESCRIPTION OF THE DRAWINGS

The method of the invention and the results of its application are illustrated in the attached drawings, in which FIG. 1 is a schematic side elevation view, partly in cross-section, showing the optical elements of the eye relative to the scanning apparatus;

FIG. 2 is a representative cross-sectional visual display prepared from the data obtained during an ultrasound scan;

FIGS. 3A and 3B are plan view illustrations of the eye graphic representations of an angle plane prepared in accordance with the method of the invention; and FIGS. 4A and 4B are, respectively, schematic cross-sectional views of the optical elements of an eye before and after surgical removal of a cataractous lens.

DETAILED DESCRIPTION OF THE PREFERRED EMBODIMENTS

Figure 5:
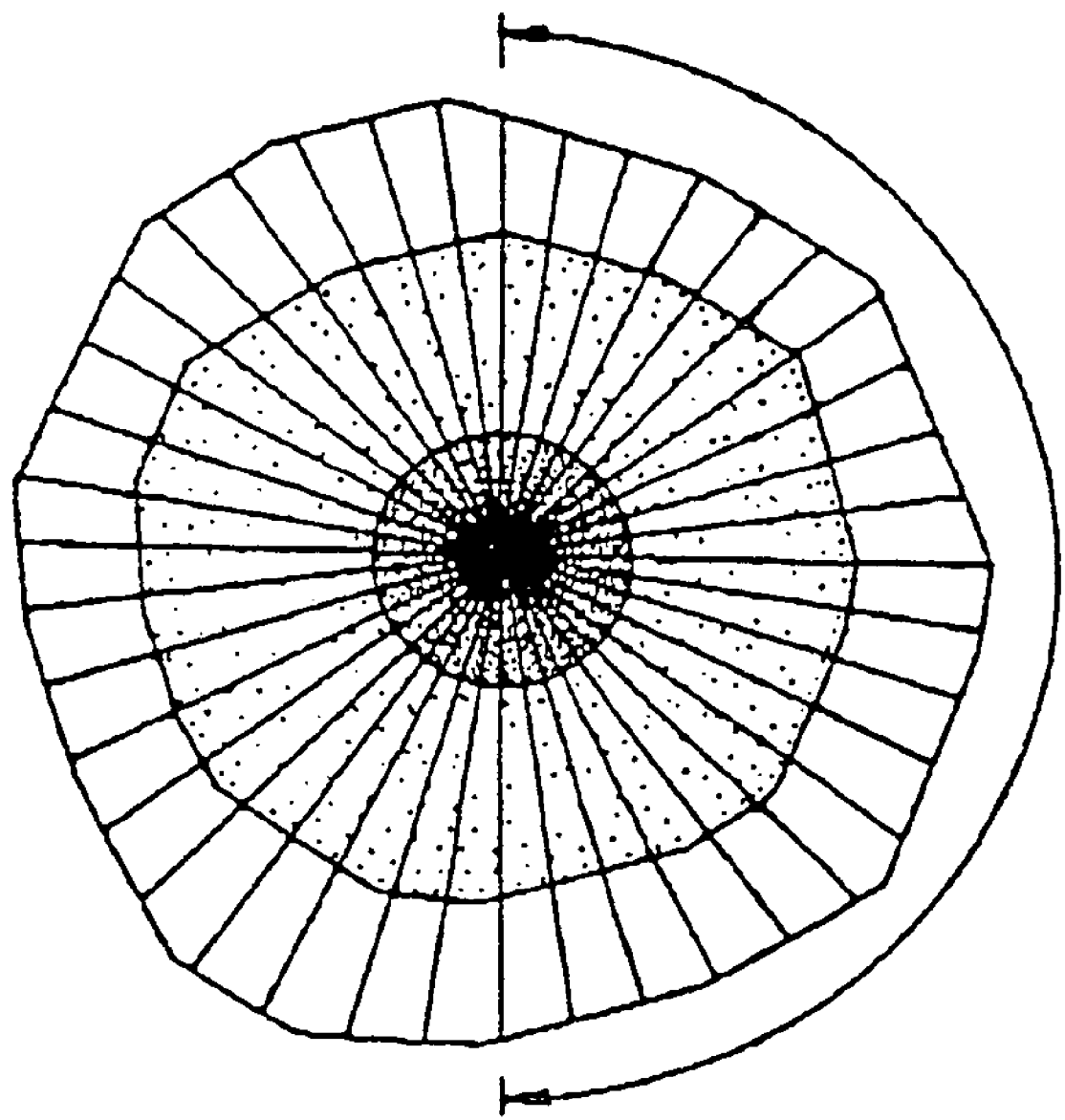
FIG. 5 is a plan view illustrating another preferred embodiment of the invention.

In the practice of the method, a very high-frequency ultrasound system 10 is utilized to precisely determine the position and configuration of the optical components of the human eye 15 by utilizing a frequency in the 50 megahertz range for the anterior segment and in the 20 megahertz range for axial length measurement.

Scans are obtained by first coupling the eye 15 to the transducer 10 using a fluid coupling medium, such as normal saline solution. The region of interest is then placed in or near the focal plane of the transducer by adjusting the range of the transducer from the eye. As shown in FIG. 1, during scanning, the transducer is ranged so that its focal plane is in or near the region of interest, i.e., the angle plane or the sulcus plane. The transducer 10 is moved as indicated by the arrow 11, and a series of range-gated pulse/echo signals 12 are obtained from one pole of the eye to the other. The dashed box 14 indicates the region from which data are obtained. The specific measurements calculated are identified in FIG. 1 as the angle-to-angle width 21, the sulcus-to-sulcus width 22 and the sulcus plane depth and the angle plane depth 23.

Ultrasound data are acquired using a focused transducer with center frequency of 30 MHz or more, e.g., about 50 MHz for the anterior segment; a frequency in the 20 MHz range can be used for axial length measurement. The higher frequency provides sufficient spatial resolution to obtain the necessary measurements required for accurate lens implant sizing, positioning and power determination. The transducer is mechanically moved across the eye. The scan plane follows a meridian or medial line passing through the center of the pupil.

During movement of the transducer, a series of acoustic pulses are emitted and echoes digitized, such that pulses are emitted at distances less than the transducer's focal zone lateral dimension, usually defined as $\lambda L/D$, where $\lambda$ is wavelength, D is transducer aperture, and L is focal length. The digitized data are then used to generate an image of the scan plane. The graphical representation of FIG. 2 is generated by displaying the angle-to-angle or sulcus-to-sulcus dimensions for a plurality of meridians passing through the center of the pupil 24 and then using conventional software to complete the particular outline depicting the geometry of the oblate shape of the angle plane 21 or sulcus plane 22. A series of scans are made in a plurality of planes so that the planes are angularly equidistant and provide complete angular coverage of the eye. In a preferred embodiment at least six scan meridian measurements are made at 30-degree intervals, where the planes are in the 12–6 o'clock (vertical with respect to the subject in a heads-up, forward-looking position). 1–7 o'clock 2–8 o'clock, 3–9 o'clock (horizontal), 4–10 o'clock and 5–11 o'clock positions.

Dimensional information is recorded for each scan plane, e.g., angle-to-angle or sulcus-to-sulcus, by use of appropriate software for this purpose. The development of the lens power and position from the software is well within the capabilities of a trained programmer of ordinary skill in the art. Specific measurements to be obtained in the practice of the invention are the anterior chamber depth, the angle-to-angle width, the sulcus-to-sulcus width, and the depth of the sulcus plane. These measurements cannot be obtained using conventional optical systems due to the opacity of the sclera and iris. The method of the invention provides advantages over other radiologic techniques such as MRI or CT that are both more expensive than ultrasound and provide lower spatial resolution.

A plurality of dimensions of the angle-to-angle width are obtained and the data recorded for use in sizing and placement of anterior chamber lens implants. Implants consist of an optic (the lens itself) and haptics which are arms extending from the optic that are provided to keep the lens centered on the pupil. Implants that are too large can cause the haptics to press against delicate adjacent tissue with resultant damage. Implanted lenses that are too small may fall out of position. In addition, because angle-to-angle width may not be the same at every meridian, the angle plane may describe an ellipse rather than a circle. Measurements of angle-to-angle dimensions along with a plurality of medial planes, or meridians, provides information for a lens prescription that is appropriate for the eye's dimensions. In addition, if the angle plane is elliptical rather than circular, the lens can be sized and implanted appropriately for the largest meridian length, which will prevent tissue damage or displacement by "propellering."

Referring to FIG. 3A, there is depicted a schematic illustration of the eye showing the pupil 30 (center) surrounded by the iris 32 and the angle-plane 34. The angle plane is not optically visible due to the presence of the opaque sclera, or white, of the eye. With reference to FIG. 3A, the lines a—a through f—f indicate scan meridians and biometric measurements of angle-to-angle width on six meridians in which the angle plane describes a circle, i.e., the angle-to-angle width is constant at all meridians. In the illustration of FIG. 3B, although the iris and pupil are round, the angle plane describes an ellipse, with its maximum dimension on the 1-to-7 o'clock medial line b—b.

For implantation of phakic lenses, i.e., implants placed between the crystalline (natural) lens and the iris, measurement of sulcus-to-sulcus dimensions are used in a method that is analogous to that described above. As shown in the illustration of FIG. 4A, the cataractous lens 40 is enlarged, resulting in shallowing of the anterior chamber 41 as indicated by the vertical arrow 42. As shown in FIG. 4B, after extraction of the cataractous lens, one surgical option is to place the implant lens 44 in the sulcus plane defined by arrow 45 in FIG. 4A where its position is maintained by haptics 46 that are placed in the sulci. Although the depth of the anterior chamber 41 changes with cataract extraction, the sulcus plane depth 48 remains constant. Preoperative measurement of sulcus plane depth 48 will allow calculation of the optimum post-operative implant position and appropriate lens power for lens 44.

The method of the invention provides the alternative of implanting a lens that can be accommodated and placed in the capsular bag that remains after extraction of the cataractous crystalline lens 40. The dimensions of the anticipated capsular bag following surgery arm calculated from the pre-operative measurement of the surface area of the capsule (lens), thereby permitting the haptic size to be optimized to the area of the flattened capsular bag.

A further preferred embodiment of the invention is illustrated in FIG. 5 where the density of medial scans is greater than the six described above. The setup of the equipment and processing of the data is substantially the same as described above, with the exception that a higher density of medial scans is undertaken. The additional scans provide data that is utilized to more precisely define non-elliptical in-plane surfaces, as are schematically represented in FIG. 5. The limitation on the number of scans is determined only by the equipment and the ability of the subject to maintain a steady position.

In a particularly preferred embodiment, a fellow eye tracking apparatus of the type used, e.g. in lasik surgical procedures, is employed during the ultrasound scanning. As will be understood by one of ordinary skill in the art, after a few seconds of scanning the subject's eyes will generally not remain stationary. Where is the number of scans is increased to 20, 40 or even 180, such eye movement is inevitable. The fellow eye tracking system will take account of any such movement in plotting the data.

Figure 6:
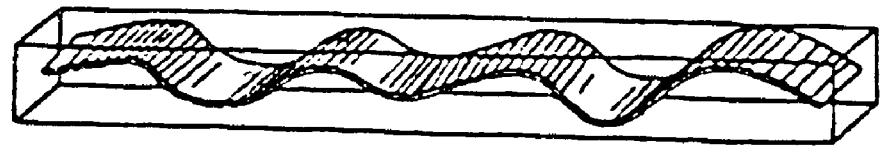
FIG. 6 is a graphic representation of trans-axial variation obtained from one preferred embodiment.

Referring to FIG. 6, there is shown schematically a graphic representation of the anterior-to-posterior variation mapping of the eye. This form of mapping can be provided when the scanning is performed in the high-density mode. With the scanning apparatus in the high-density mode, angle or sulcus in-plane, (e.g., across the eye), and trans-axial (from the front to the back of the eye) variability can be mapped with splines, B-splines or other formulations. individual sector scans which extend only between the outer concentric dotted lines. The intermediate concentric ring formed of broken lines represents a plot of the outermost points along the margin of the plane being plotted.

Because of the relatively short length of each individual scan in the margin sector, they are of much shorter duration than the scans described above in connection with FIGS. 3A, 3B and 5 that traverse the entire width of the respective portions of the eye.

Figure 7:
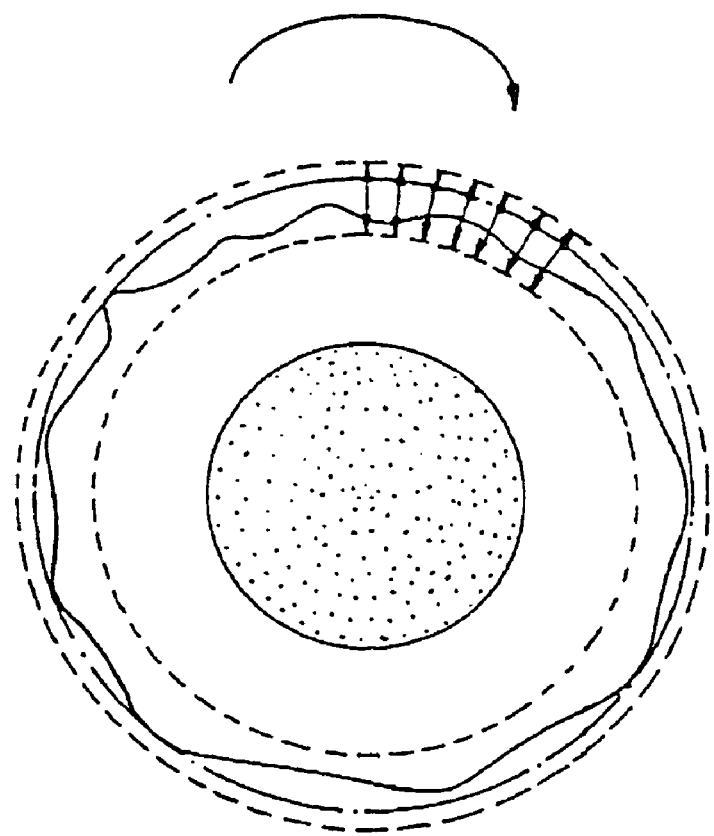
FIG. 7 is a schematic plan view of the eye showing alternative method of scanning.

In the practice of this method, a mechanical sector scanner or beam-steered array is coupled to the arc scanner. In this embodiment, the scanner acquires data in a single circumferential path, indicated by the direction of the arrow, which in the illustration of FIG. 7 is clockwise.

The marginal sector scanning method described above and illustrated in FIG. 7 can also be utilized to scan a particular marginal sector, e.g., a 30°–60° arc, as distinguished from the entire 360° marginal edge of the desired plane or planes. For example, the event that the data obtained from a series of six scans described in connection with FIGS. 3A and 3B, above, indicated a significant anomaly in one sector, that sector alone can be subjected to a marginal scan to reveal its conformation in more detail. This method can thus be practiced after the more limited number of meridional coronal scans have been completed and the data processed and displayed, and while the subject is still in position relative to the apparatus.

The successful use of toric intraocular lens implants for correction of astigmatism in both the intact and post-intra-capsular cataract extract eye, is dependent on precise lens alignment with the astigmatic axis. Lens propellering, a common post-surgical complication necessitating surgical revision, is caused by misalignment of the intra-ocular lens haptic supports and at the conformal surface of the angle or the sulcus. In accordance with the invention, measurements of the elliptical surface of the angle and sulcus confirms their relationship with the axis of accommodation.

Using the data from six hemispheric scans, anamorphically corrected biobetric angle-to-angle and sulcus-to-sulcus measurements are modeled using the direct least-squares method. The data is constrained to an ellipse. Additional scans can be performed, e.g., up to twenty scans, or more, in order to obtain a more precise depiction of the perimeter of the angle surface. The data is evaluated utilizing standard circular and directed statistic techniques.

When the method of the invention is utilized to determine the semi-major axis, it was found to be more accurate than the refractive or the keratometrically determined axis of astigmatism. Thus, the method has utility in providing a more accurate correction to subject's vision through both the characteristics of the corrective lens and the placement of the lens in the subject's eye.

As will be understood by those of ordinary skill in the art, the method of the invention is utilized to obtain post-operative measurements in order to determine whether any long-term hazards exist to the iris, i.e., glaucoma hazard, or to the lens, i.e., cataract hazard.

As will be apparent to one of ordinary skill in the art from the above descriptions of the preferred embodiments, the higher resolution and particularly the three-dimensional representations produced by the practice of the method of the invention provide greater accuracy in the determination of the appropriate lens power for post-cataract surgical correction and for lens implantation in phakic eyes of patients.

We claim:

1. A method of producing for visual display a representation of the geometry or the topography, or both the geometry and topography of a portion of the eye of a subject which representation is based on data generated by an ultrasound scan of the optical components of the eye, the method comprising the steps of:
    a. providing a very high-frequency ultrasound scanning apparatus that includes a programmed computer and ancillary data storage device;
    b. positioning the subject's eye relative to the apparatus for scanning;
    c. scanning the subject's eye to thereby generate data representative of a plurality of angularly-spaced meridional sections taken across the entire coronal plane of the anterior surface of the eye;
    d. collecting and storing the data obtained in step (c) in the ancillary data storage device;
    e. processing the coronal scan data; and
    f. generating for visual display a representation of a portion of the geometry or topography, or both the geometry and topography of a portion of the subject's eye.

2. The method of claim 1, wherein the processing of the coronal scan data includes the steps of:
    identifying the longest coronal meridian and a plurality of other coronal meridians in one or more optical planes; and
    generating a graphic display of the coronal meridians indicating their relative lengths across the one or more optical planes.

3. The method of claim 1, wherein the processing of the coronal scan data includes the steps of:
    generating meridional measurements that includes one or more characteristics selected from the sulcus plane depth, the angle-to-angle width and the sulcus-to-sulcus width.

4. The method of claim 3, wherein the visual representation includes all three of the characteristics.

5. The method of claim 1, wherein the representation is printed for visual display.

6. The method of claim 1, wherein the representation is visually displayed on a monitor.

7. The method of claim 1, wherein at least six angularly spaced coronal section scans are performed.

8. The method of claim 7, wherein multiple equally-spaced scans are performed.

9. The method of claim 1, wherein the angular displacement between the scans are approximately equal.

10. The method of claim 9, where the angular displacement between each of the scans is from 30° to 1°.

11. The method of claim 1, which further comprises:
    providing a fellow eye tracking device;
    operatively connecting the fellow eye tracking device to the ultrasound scanning apparatus and the data storage device; and
    positioning the eye of the subject that is not being scanned relative to the tracking device.

12. The method of claim 11, wherein the angular displacement between each scan is 20° or less.

13. A method of producing for visual display a representation of the geometry or the topography, or both the geometry and topography of a portion of the eye of a subject, which representation is based on data generated by an ultrasound scan of the optical components of the eye, the method comprising the steps of:
    a. providing a very high-frequency ultrasound scanning apparatus that includes a programmed computer and ancillary data storage device;
    b. positioning the subject's eye relative to the apparatus for scanning;
    c. scanning the subject's eye to thereby generate data representative of a plurality of angularly-spaced sections taken across a marginal portion of the coronal plane of the anterior surface of the eye;
    d. collecting and storing the data obtained in step (c) in the ancillary data storage device;
    e. processing the sectional scan data; and
    f. generating for visual display a representation of a portion of the geometry or topography, or both the geometry and topography of a portion of the subject's eye.

14. The method of claim 13, wherein the margin portion is defined by a pair of concentric boundaries disposed on either side of the terminii of the maximum coronal meridian of the eye of the subject.

* * * * *